(12) United States Patent
Anglada et al.

(10) Patent No.: US 9,549,836 B2
(45) Date of Patent: Jan. 24, 2017

(54) ORTHOSIS FOR TREATING RHIZARTHROSIS

(75) Inventors: Gerard Anglada, Saint Etienne (FR); Thomas Beckers, Gardabaer (IS)

(73) Assignee: GIBAUD, Saint Etienne (FR)

( * ) Notice: Subject to any disclaimer, the term of this patent is extended or adjusted under 35 U.S.C. 154(b) by 903 days.

(21) Appl. No.: 13/384,403

(22) PCT Filed: Jul. 15, 2010

(86) PCT No.: PCT/FR2010/051489
§ 371 (c)(1),
(2), (4) Date: Mar. 26, 2012

(87) PCT Pub. No.: WO2011/007103
PCT Pub. Date: Jan. 20, 2011

(65) Prior Publication Data
US 2012/0179081 A1    Jul. 12, 2012

(30) Foreign Application Priority Data

Jul. 17, 2009  (FR) ...................................... 09 03534

(51) Int. Cl.
*A61F 5/01*    (2006.01)
(52) U.S. Cl.
CPC .................................... *A61F 5/0118* (2013.01)
(58) Field of Classification Search
USPC ............. 128/877–880; 602/5, 20–22, 60–64; 2/158–161.8
See application file for complete search history.

(56) References Cited

U.S. PATENT DOCUMENTS

| | | | | |
|---|---|---|---|---|
| 5,771,901 A * | 6/1998 | O'Brien | ......................... | 128/878 |
| 5,899,870 A * | 5/1999 | Deirmendjian et al. | ......... | 602/21 |
| 6,427,246 B1 * | 8/2002 | Doi | .................. | A41D 19/01588 2/159 |
| 6,475,174 B1 * | 11/2002 | Chow | .............................. | 602/5 |
| 6,496,984 B1 * | 12/2002 | Chow | ................... | A61F 5/0118 2/16 |
| 7,377,566 B2 * | 5/2008 | Gazaui | ...................... | B65G 7/12 294/137 |
| 7,645,250 B2 * | 1/2010 | Koby et al. | ..................... | 602/21 |
| 7,887,497 B2 * | 2/2011 | Weber et al. | ................... | 602/21 |
| 2009/0240182 A1 * | 9/2009 | Weber | ................... | A61F 5/0118 602/21 |

FOREIGN PATENT DOCUMENTS

| | | |
|---|---|---|
| FR | 2 822 371 | 9/2002 |
| FR | 2 854 564 | 11/2004 |
| WO | 2006117808 A1 | 11/2006 |

OTHER PUBLICATIONS

International Search Report issued in PCT/FR2010/051489, dated Dec. 7, 2010.

* cited by examiner

*Primary Examiner* — Ophelia A Hawthorne
(74) *Attorney, Agent, or Firm* — Workman Nydegger

(57) ABSTRACT

An orthosis to be placed on the hand of a user, including a supporting member having the general shape of a horse saddle and having an inner flange and an outer flange, to be placed at the thumb-index commissure with the inner flange against the palm and the outer wing against the back surface of the hand, in order to enable a spacing to be maintained between the thumb and the index finger. The orthosis includes a strap to be placed around the hand and the supporting member so as to retain said supporting member such that the metacarpal bone of the thumb is trapped inside the orthosis between the strap and supporting member.

19 Claims, 6 Drawing Sheets

ORTHOSIS FOR TREATING RHIZARTHROSIS

CROSS REFERENCE TO RELATED APPLICATIONS

This application is the national stage application of PCT/FR2010/051489, filed Jul. 15, 2010, and claims the benefit of priority of French application no. 0903534, filed Jul. 17, 2009, the contents of both of which are incorporated by reference herein in their entirety.

BACKGROUND

The present invention relates to an orthosis intended to be placed on the hand of a user, in particular to treat rhizarthrosis.

Rhizarthrosis—or arthrosis of the base of the thumb—is the wear of the cartilage of the joint at the base of the thumb, between the trapezius and the metacarpal bone. Aside from the pain it causes, this pathology can cause joint stiffness and deformation of the thumb, preventing the grasping of an object between the thumb and the index or other fingers. There is also a risk of luxation of the joint.

Orthopedic treatment of rhizarthrosis aims on the one hand to decrease pain, and on the other hand to prevent the loss of range of movement, i.e. the impossibility of moving the thumb away from the index finger.

Several types of orthoses of the hand used to treat rhizarthrosis are already known.

According to a first known embodiment, such an orthosis consists of a rigid piece made from a thermoformable material. The intervention of an orthotist is generally required to customize this piece. An orthosis of this type is therefore restrictive and expensive to produce. Furthermore, it cannot be easily adapted to wearing conditions, typically daytime wear and nighttime wear.

According to a second known embodiment, such an orthosis consists of a textile strap, possibly provided with stiffeners, that the user winds and fastens around his hand. This orthosis is generally difficult for the user to place alone. Furthermore, poor positioning can be detrimental to the orthopedic treatment.

Another hand orthosis to treat rhizarthrosis is proposed in document WO 2006/117808. The orthosis described in this document has a certain number of drawbacks.

First of all, it is fairly difficult to place, in particular when it involves positioning the additional band surrounding the finger, which is necessary to maintain the piece on which the thumb rests.

Furthermore, in order to obtain effective immobilization of the area of the lesion, this orthosis blocks other zones, whereas this is not directly necessary for the concerned pathology. This in particular involves the distal part of the thumb, the base of the long fingers, and an extended area around the joint of the wrist. This causes a significant limitation of the movements of the hand, which makes the orthosis fairly uncomfortable and impractical, and may dissuade some people from wearing it.

SUMMARY

The present invention aims to resolve the aforementioned drawbacks by providing a comfortable orthosis that is easy to use, effective, and advantageously configurable.

To that end, the orthosis according to the invention comprises:

a supporting member having the general shape of a horse saddle and having an inner flange and an outer flange connected by a curved U-shaped junction band, the supporting member being arranged to be able to be placed at the thumb-index commissure with the inner flange against the palm and the outer flange against the back surface of the hand, the junction band bearing on the one hand on the proximal phalange of the thumb and on the other hand on the proximal phalange of the index finger in order to enable a spacing to be maintained between the thumb and the index finger;

a strap to be placed around the hand and the supporting member, so as to retain said supporting member, the orthosis being arranged such that the metacarpal bone of the thumb is trapped inside the orthosis between the strap and the supporting member.

In this way, the supporting member ensures a spacing between the thumb and the index finger that procures an antalgic effect and preserves the range of motion. Furthermore, the strap creates, combined with the supporting member, bearing on either side of the hand that immobilizes the osteoarticular column of the thumb and prevents the luxation of the joint.

Owing to the orthosis according to the invention, the metacarpal bone of the thumb is immobilized in all directions, i.e.:

on the one hand in the direction bringing the thumb closer toward the index finger, using the horse saddle-shaped supporting member. This member forms a U-shaped groove open toward the wrist that bears on the bottom of the commissure, and surrounds the proximal phalange of the thumb and at least the proximal part of the proximal phalange of the index finger, thereby limiting the movement of the thumb. Furthermore, these phalanges are locally held captive between the junction band and the flanges of the supporting member;

on the other hand, in the direction of the pronosupination, using the strap and the supporting member, owing to which the metacarpal bone is sandwiched.

The fact that the metacarpal bone is trapped and immobilized in the orthosis according to the invention has many advantages.

In particular, the orthosis makes it possible to immobilize the trapeziometacarpal joint, which is the seat of the lesion, and thereby to directly obtain the desired effect. The direct immobilization of the area of the lesion means that it is not necessary to immobilize other areas of the hand.

Thus, on the one hand, it is not necessary also to provide a circular band surrounding the thumb. As a result, the orthosis according to the invention is easier to place, tourniquet risks are avoided, the column of the thumb is freed, and the pulp of the thumb is also freed—which is quite significant for users, who preserve the sense of touch in their daily lives.

On the other hand, the strap of the orthosis according to the invention can be less enveloping, and in particular free the base of the long fingers, therefore not hindering their movement, in particular their extension.

In practice, according to a first embodiment, the supporting member is simply placed in the thumb-index commissure and, if applicable, pressed against it, then the strap is enveloped around the hand and the supporting member. The placement of the orthosis is particularly simple and without risk of poor positioning, due in particular to the ergonomic shape of the supporting member. The combination of the supporting member and the strap ensures good effectiveness of the orthosis without harming wearer comfort.

According to a second embodiment, the supporting member is already associated with the strap, the latter forming a sleeve that slides on like a glove. After sliding onto the hand, a free part of the strap is folded down against the back surface of the hand with the appropriate tightening.

Advantageously, the supporting member and the strap are two separate pieces. In this way, the orthosis is configurable. In fact, the supporting member being removable, the strap can be used alone, for example for daytime wear.

According to one possible embodiment, the inner flange of the supporting member is outwardly curved toward the free end thereof. The flared shape of the outer flange favors the placement of the supporting member between the thumb and the index finger. Furthermore, this makes it possible to reinforce the bearing against the palm of the hand, through the elasticity thus procured by the supporting member.

The supporting member can be made from a flexible material, such as silicone or SEBS (styrene ethylene butylene styrene). It is then particularly comfortable, while having the strength necessary for its function, in particular for spacing of the thumb. Furthermore, it can hug the shape of the commissure and ensure good bearing in the hollow area between the thumb and the index finger.

Alternatively or complementarily, the supporting member can comprise a rigid U-shaped piece situated substantially at the junction between the inner and outer flanges, said U-shaped piece being able to be deformed so as to modify the spacing between the thumb and the index finger depending on the user's morphology. The supporting member can for example be molded around said U-shaped piece.

Furthermore, the orthosis can include a rigid rod associated with the supporting member and/or the strap such that, in the usage position, said rod extends over the back surface of the hand substantially in the extension of the outer flange of the supporting member and creates bearing against the back surface of the hand. The bearing created by this rod allows very good support of the metacarpal, thereby preventing the luxation of the joint. This dorsal rod, which is preferably fitted into the supporting member, completes the trapping of the metacarpal and the proximal phalange of the thumb in the orthosis. This rod, maintained on the hand by a strap, prohibits the bending, extension, radial incline, and cubital incline movements.

Advantageously, the rigid rod can be made from a deformable material such that a person can bend or curve it so as to place the wrist slightly flexed, in the usage position of the orthosis. Depending on the needs, the wrist may be placed in the palmar flexion or dorsiflexion. The rod is for example made from aluminum.

It is possible to provide that the supporting member comprises a housing formed in its outer flange and intended to receive an end portion of the rigid rod. The other end portion of the rod can be situated in a housing formed in the strap or, alternatively, can simply be trapped between two faces of the strap.

According to one possible embodiment, the strap, when flat, is substantially in the shape of a T that has first and second branches substantially one in the extension of the other intended to surround the hand while being folded down against the back surface of the hand, and the third branch intended to be folded toward the back surface of the hand while passing through the thumb-index commissure and covering the supporting member. The third branch makes it possible to adjust the pressure of the supporting member. Furthermore, this T shape makes it possible to free the back surface of the hand by freeing the metacarpophalangeals of the middle finger, the ring finger, and the pinky finger.

Furthermore, the strap can have a sufficient size to also surround the wrist, in the usage position. The immobilization of the wrist makes it possible to create a significant lever arm, which improves the effect of the orthosis on the rhizarthrosis. This can in particular be used during nighttime wear, while a shorter strap, leaving the wrist free, can be used for daytime wear.

The strap can comprise at least one stiffening element which, in the usage position, extends over the back surface of the hand substantially in the extension of the outer flange of the supporting member. This can for example be a rib engaged in a sheath of the strap. This makes it possible to create additional bearing against the back surface of the hand.

Advantageously, the orthosis can be arranged so that, when it is worn by a user, the hand of the user equipped with the orthosis has a slight cubital incline, which makes it possible to decrease the tension of the wrist muscles. This effect can be obtained using the aforementioned rigid rod.

The orthosis can also comprise a rigid strip associated with the strap, said strip extending, in the usage position, from the inner side of the hand and forearm substantially along the axis of the forearm, having a sufficient length to extend on either side of the wrist joint, and having a curved shape fitting the relief of the wrist and the palm of the hand. This palmar strip makes it possible to complete the immobilization action of the wrist and the column of the thumb.

The combination of the supporting member, the dorsal rod, and the palmar strip, associated with the strap, offers particularly effective immobilization using three bearing points.

BRIEF DESCRIPTION OF THE DRAWINGS

We will now describe, as non-limiting examples, several possible embodiments of the invention, in reference to the appended figures.

DETAILED DESCRIPTION OF VARIOUS EMBODIMENTS

An orthosis 1 according to the invention, as illustrated in FIGS. 8 to 11, comprises a supporting member 2 and a strap 3.

Figure 1:
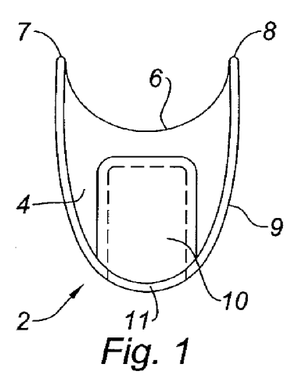
FIGS. 1 to 3 show a supporting member belonging to the orthosis according to the invention, in an outer view, inner view, and side view, respectively.
Figure 2:
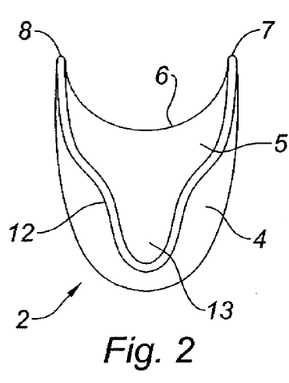
Figure 3:
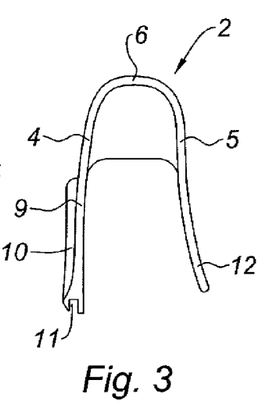

The supporting member 2, illustrated in FIGS. 1 to 3, assumes the general shape of a horse saddle (substantially hyperbolic paraboloid shape). In this way, it has an outer flange 4 and an inner flange 5 opposite one another connected by a junction band 6 having a curved U shape from one end edge 7 to the other 8.

The outer flange 4 is generally flat and has a free edge 9 in the shape of a U joining the two end edges 7, 8 of the junction band 6. According to one possible embodiment, the outer flange 4 also comprises a housing 10 protruding toward the outside of the supporting member 2 and having an opening 11 opposite the junction band 6.

The inner flange 5 has a free edge 12 that joins the two end edges 7, 8 of the junction band 6 and comprises a central tab 13. The inner flange 5 is generally parallel to the outer flange 4 while being curved outwardly from the junction band 6 toward its free end, as shown in FIG. 3.

Figure 4:
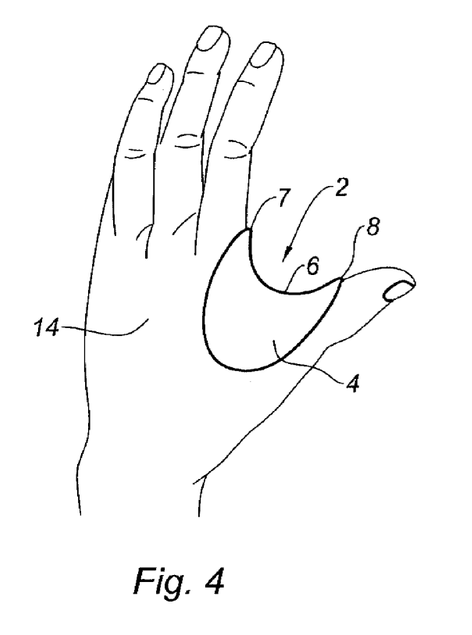
FIGS. 4 and 5 show the supporting member placed on the left hand of the user, in outer view and inner view, respectively.
Figure 5:
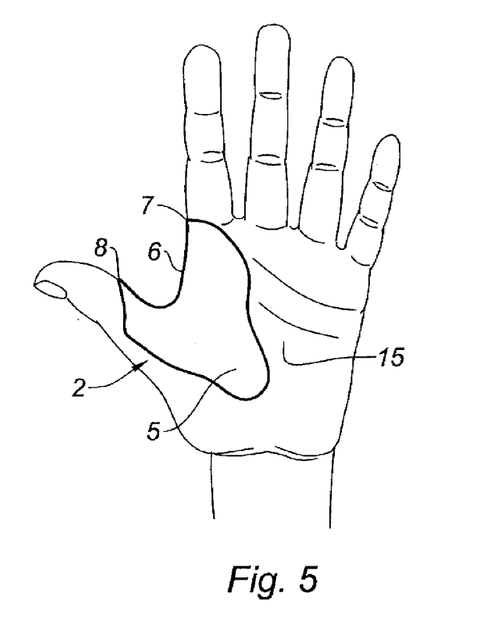

The supporting member 2 is placed on the hand of a user as illustrated in FIGS. 4 and 5. The supporting member is engaged between the thumb and index finger, on either side of the hand, the flared shape of the inner flange 5 facilitating this placement, until the junction band 6 rests substantially on the thumb-index commissure. The hand is then gripped between the outer flange 4, against the back surface 14 of the hand, and the inner flange 5, against the palm 15 of the hand. Furthermore, the junction band 6 bears on the one hand on the proximal phalange of the thumb, and on the other hand on the proximal phalange of the index finger, the supporting member 2 forming a channel that partially surrounds said phalanges. In this way, the supporting member 2 makes it possible on the one hand to guarantee spacing between the thumb and the index finger, and on the other hand to ensure pressure on either side of the hand, accentuated by the flared shape of the inner flange 5.

In the illustrated embodiment, the supporting member 2 is made from a flexible material, such as silicone or SEBS (styrene ethylene butylene styrene). As a result, while having the strength necessary for its function of maintaining the spacing, the supporting member 2 can be elastically deformed to adapt to the commissure and fit the shape thereof.

Figure 6:
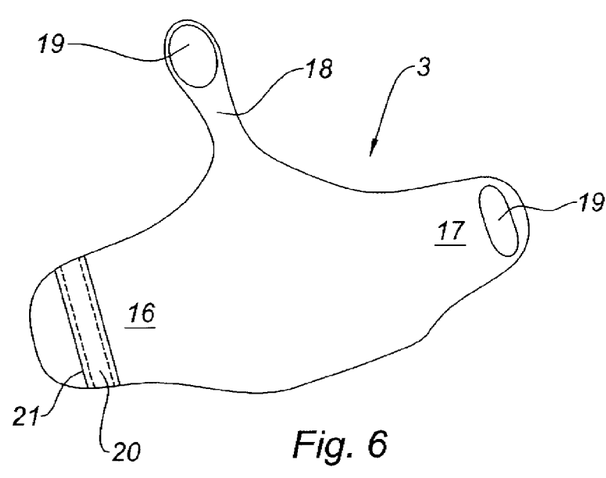
FIG. 6 is a flat diagrammatic view of a strap belonging to the orthosis according to the invention.

We will now describe the strap 3 in reference to FIG. 6.

The strap 3, flat, substantially assumes the shape of a T that has first and second branches 16, 17 substantially in the extension of one another, and a third branch 18 orthogonal to the branches 16, 17. Advantageously, the strap 3 is made from a 3D mesh fabric allowing comfort and breathability. The end portion of the second and third branches 17, 18 is provided with a catching zone 19 of the Velcro® type. The absence on the strap of a tightening branch compressing the trapeziometacarpal is also an important element in improving the wearing comfort of the orthosis 1.

Furthermore, the strap 3 can comprise a rib 20 engaged in a sheath 21 provided at the first branch 16, substantially parallel to the third branch 18. In this way, when the strap 3 is placed on the hand, the rib 20 extends on the back surface 14 of the hand substantially in the extension of the outer flange 4 of the supporting member 2.

Figure 7:
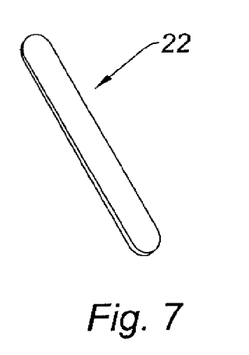
FIG. 7 is a perspective view of a rigid rod that can belong to the orthosis according to the invention.

The orthosis 1 can also comprise a rigid rod 22 having a flat and elongate shape as illustrated in FIG. 7. The rigid rod 22 is for example made from aluminum.

In practice, the placement of the orthosis 1 on the hand is done as follows. First, the supporting member 2 is placed at the thumb-index commissure as explained above and as illustrated in FIGS. 4 and 5. The rigid rod 22 is inserted into the housing 10 formed on the outer flange 4 of the supporting member, so that it can extend over the back surface 14 of the hand substantially in the extension of the outer flange 4 of the supporting member 2.

The strap 3 is then placed around the hand and the supporting member 2. The first and second branches 16, 17 are folded down from the palm 15 against the back surface 14 of the hand, so as to surround the hand, while the third branch 18 is folded down from the palm 15 toward the back surface 14 of the hand, passing through the thumb-index commissure and covering the supporting member 2 (see FIG. 8). The catching zones 19 make it possible to close the strap 3 and to adjust the tightening. Having a single strap greatly facilitates the placement of the orthosis.

In this position, the strap 3 ensures the retention of the supporting member 2 against the thumb-index commissure and presses the rigid rod 22 against the back surface 14 of the hand. The metacarpal bone of the thumb is thus trapped in the orthosis 1 between the strap 3 and the supporting member 2, whether in the plane of the fingers, in the direction moving further away from or closer to the index finger, or in the direction perpendicular to this plane, toward the palm or toward the back surface of the hand. An additional bearing is created by the rigid rod 22.

The rigid rod 22 can be kept straight, so as to keep the wrist in the resting position (aligned with the arm), or can be deformed, so as to place the wrist in a raised (dorsiflexion) or bent (palmar flexion) position.

The orthosis 1 is configurable and adaptable both to the morphology of the user and the wearing time.

In fact, for nighttime wear, it is preferable to use a long strap, immobilizing the wrist, and to wear the supporting member 2. As a result, at night, the orthosis 1 keeps the thumb in a spaced position, thereby preserving the range of motion, which makes it possible to keep normal use of the thumb during the day. As a result, during daytime wear, the strap 3 can be used alone, i.e. without the supporting member 2. It is also possible to use a short strap, leaving the wrist free.

Figure 11:
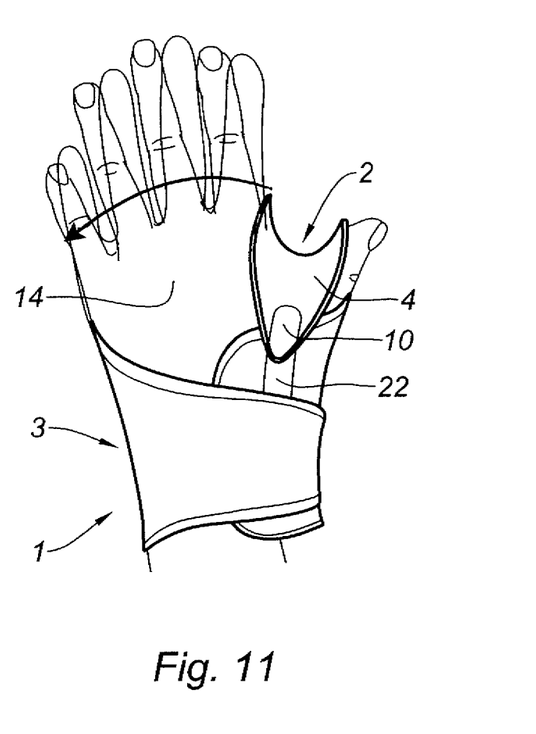
FIG. 11 is an outer view of the left hand of a user equipped with the orthosis, showing the cubital incline of the hand.

FIG. 11 shows that the hand equipped with the orthosis 1 according to the invention is advantageously placed at a slight cubital incline. For example, it is the straightness of the rigid rod 22 that maintains this cubital incline, thereby decreasing the tension of the wrist muscles.

Figures 8, 9:
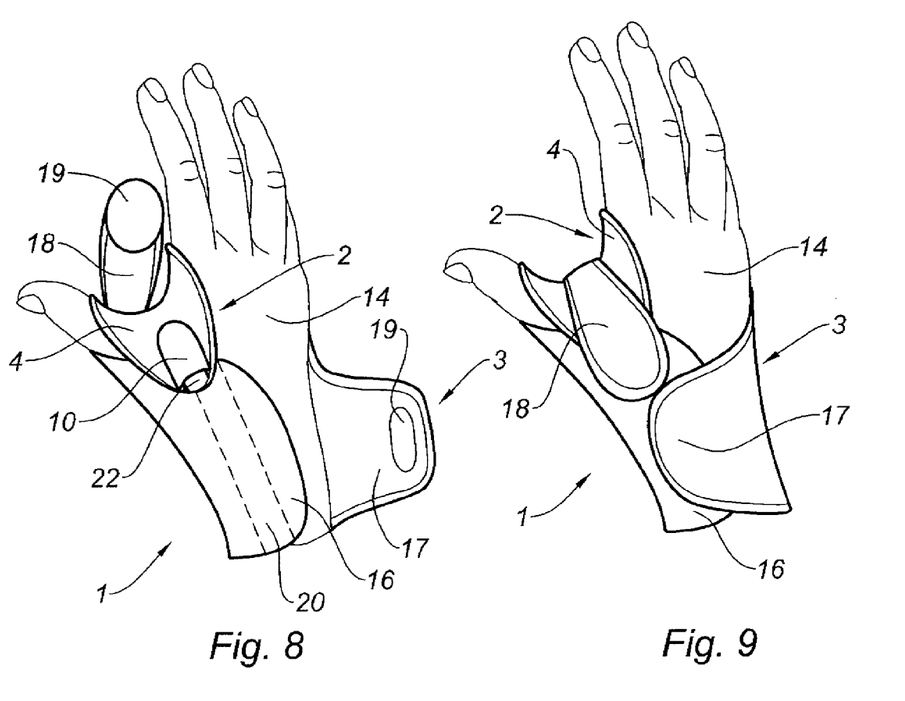
FIG. 8 is an outer view of the right hand of a user equipped with the supporting member, with the strap during placement.
FIGS. 9 and 10 are views of the hand of a user equipped with the orthosis, the right hand in outer view and the left hand in inner view, respectively.
Figure 10:
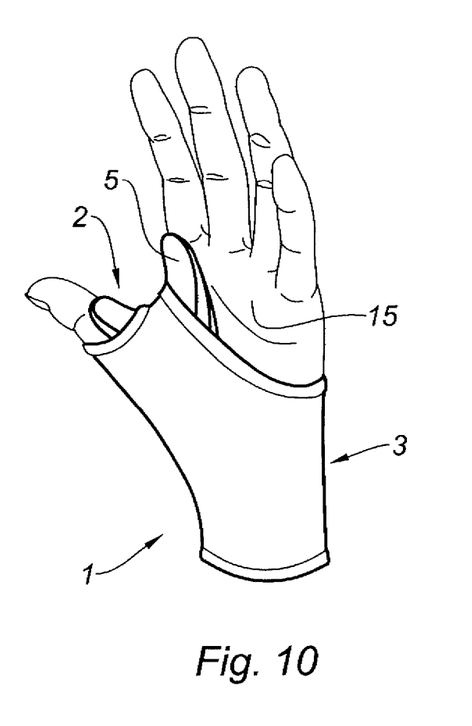

Furthermore, as shown in FIGS. 9 and 11, the orthosis 1 according to the invention (i.e. the supporting member 2, the strap 3, and possibly the rigid rod 22) may be placed on the left or right hand.

Figure 12:
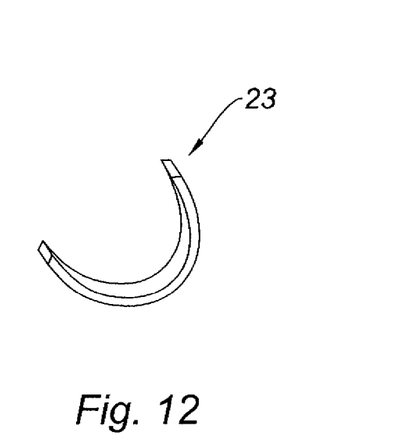
FIG. 12 is a perspective view of a rigid U-shaped piece that can belong to the orthosis according to the invention.
Figure 13:
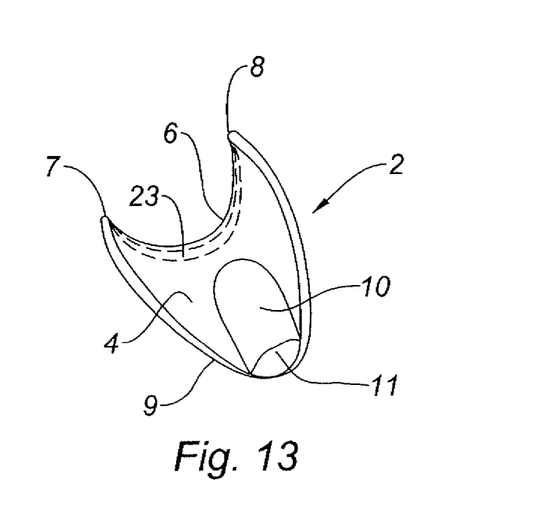
FIG. 13 shows a supporting member comprising the rigid U-shaped piece of FIG. 12.

According to one alternative of the invention, the supporting member 2 comprises a rigid U-shaped piece 23 as illustrated in FIG. 12. This piece 23 is for example made from aluminum, and the supporting member is molded around said piece 23, as shown in FIG. 13. The piece 23 is situated substantially at the junction between the inner and outer flanges 5, 4, following the shape of the junction band 6. The piece 23 can be deformed so as to modify the spacing between the thumb and the index finger depending on the morphology of the user or the seriousness of the rhizarthrosis. The supporting member 2 can then perfectly fit the shape of the commissure.

Figure 14:
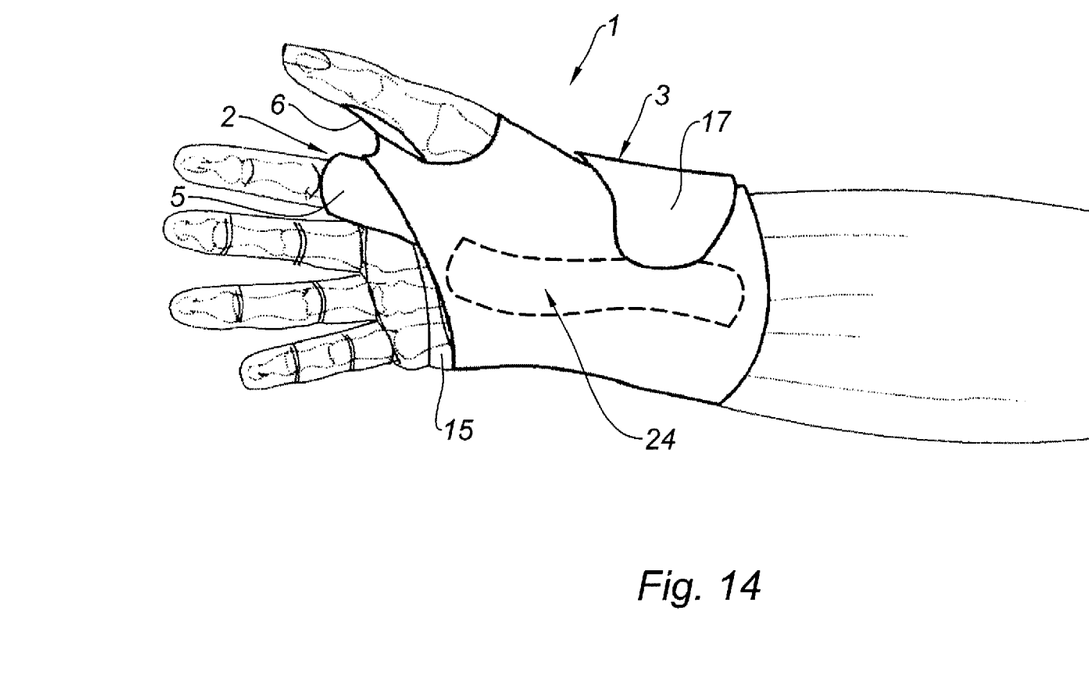
FIG. 14 is an inner view of the right hand of a user equipped with the orthosis also provided with a rigid strip.
Figure 15:
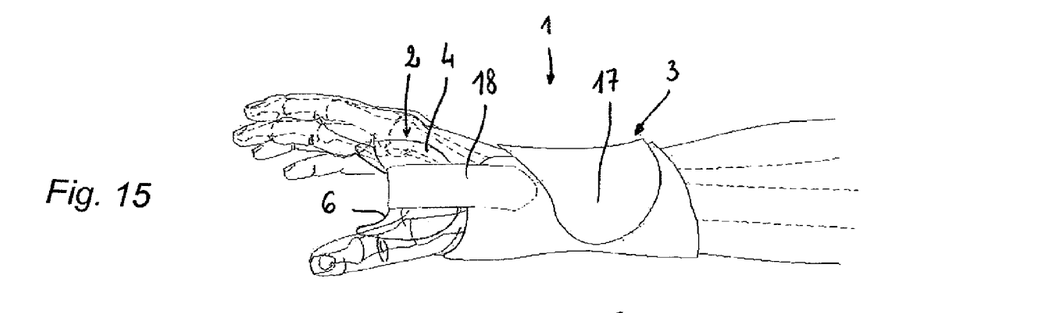
FIGS. 15 to 18 are different views of the right hand of a user equipped with an orthosis according to the invention.
Figure 16:
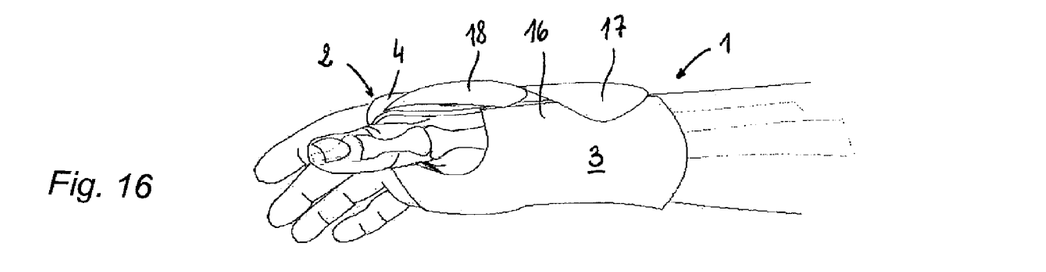
Figure 17:
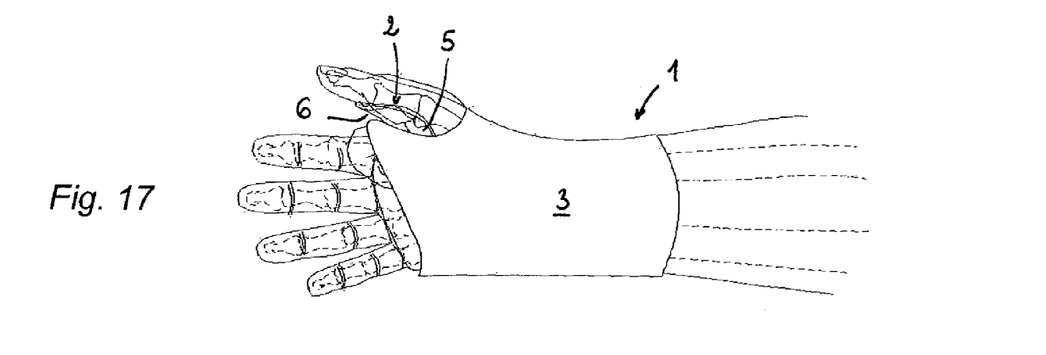

As illustrated in FIG. 14, the orthosis 1 according to the invention can also comprise a rigid strip 24 associated with the strap 3. In the usage position, this strip 24 extends from the lower side of the hand and the forearm substantially along the axis of the forearm. The strip 24 has a sufficient length to extend on either side of the wrist joint, and has a curved shape fitting the relief of the wrist and of the palm of the hand.

The strip 24 makes it possible to improve the immobilization of the wrist. It is preferably made from aluminum, so as to be able to be shaped manually to place the wrist in palmar flexion or in dorsiflexion.

Figure 18:
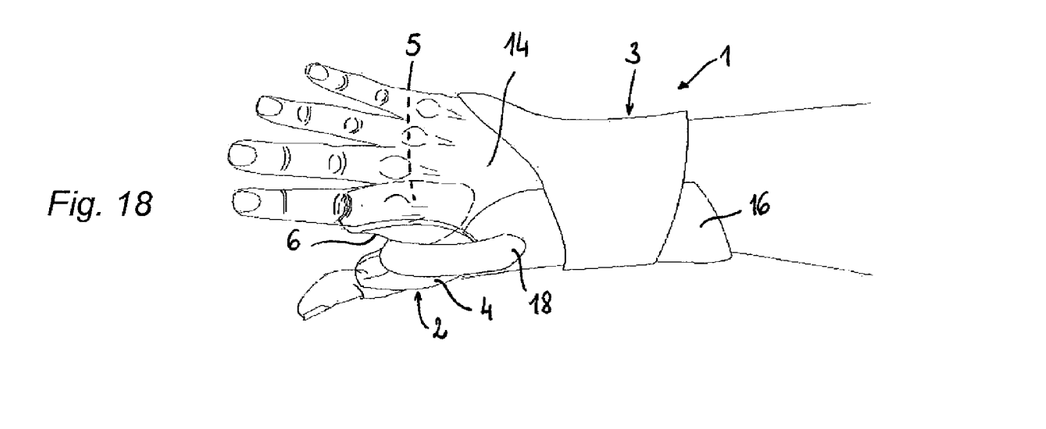
Figure 19:
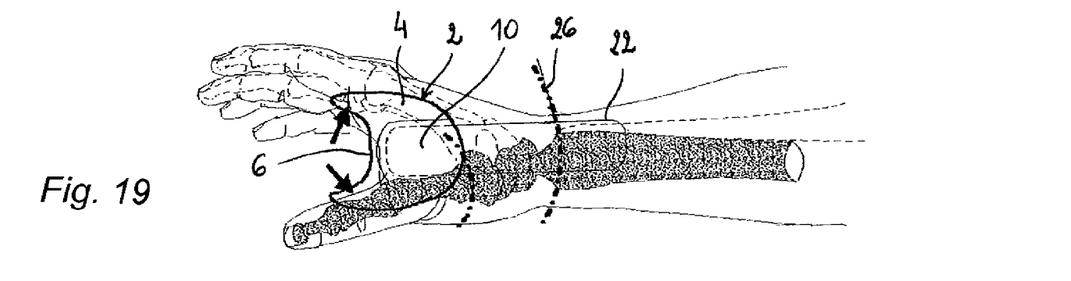
FIGS. 19 to 22 are views similar to FIGS. 15 to 18, respectively, the strap of the orthosis not being shown.
Figure 20:
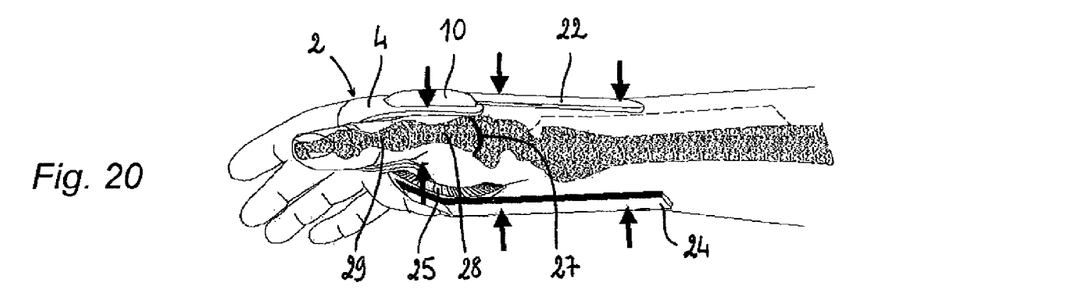
Figure 21:
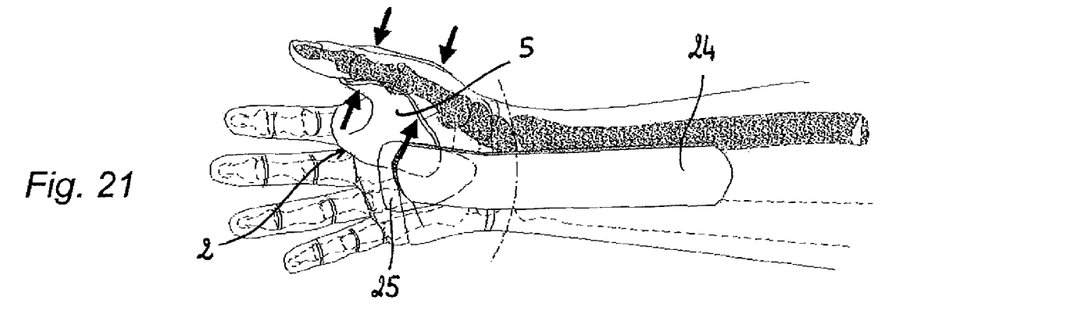
Figure 22:
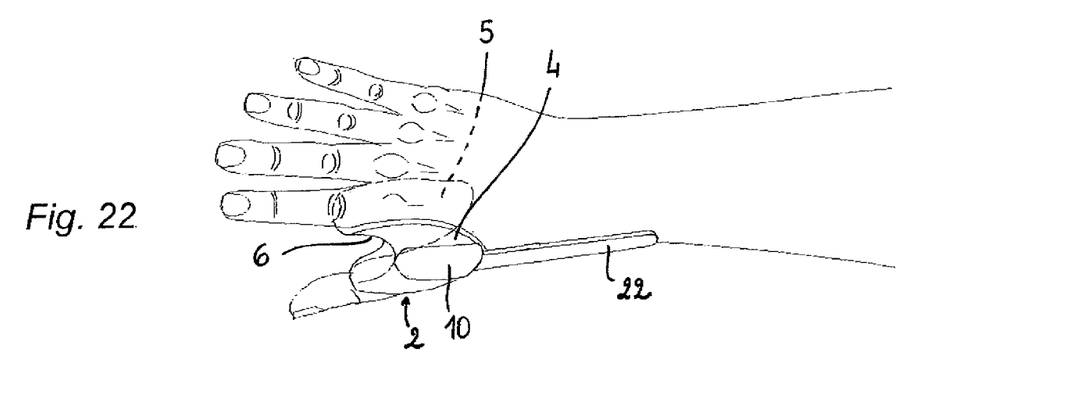

We will now refer to FIGS. 15 to 22, which clearly show the immobilization effect procured by the orthosis 1. The arrows of FIGS. 19 to 21 show the bearing that contributes to this immobilization. In particular, FIG. 19 illustrates the maintenance of the commissure opening and FIG. 20 illustrates the trapping of the column of the thumb between the dorsal rod 22 and the palmar strip 24.

In these figures, the orthosis 1 also comprises a palmar pad 25. This is an optional element that makes it possible to fill in the hollow space between the palm of the hand and the strap 3—typically between the palm of the hand and the palmar strip 24—and therefore to improve comfort.

As shown in particular in FIGS. 19 and 20, the orthosis 1 procures trapping of the wrist (axis 26 of the wrist joint), of the trapeziometacarpal 27, which is the seat of the lesion, of the metacarpal 28 of the thumb, and of the proximal phalange 29 of the thumb.

In this embodiment comprising the pad 25, the immobilization of the trapeziometacarpal and the wrist is obtained by the junction of the palmar pad 25 fixed on the palmar strip 24 and the supporting member 6 fixed on the dorsal rod 22.

When the thumb is in the resting position, it is situated in the extension of the forearm, which allows continuity between the wrist and the column of the thumb.

Furthermore, in FIG. 18, it is visible that the back surface 14 of the hand is greatly freed, which preserves the movement of the long fingers.

Thus, the invention provides a decisive improvement to the prior technique, by supplying an orthosis that is particularly simple to place. It in fact suffices to place, if applicable, the supporting member in a position overlapping the thumb-index commissure, then to wind the single strap around the hand. Furthermore, the orthosis is adapted to the morphology of the user owing to the flexible supporting member. The orthosis is also configurable on the one hand due to its left-right symmetry, and on the other hand due to the optional placement of the supporting member, the strap being able to be used alone.

The orthosis allows just the necessary immobilization of the concerned segments, i.e. the immobilization of the osteoarticular column of the thumb, but leaves the freedom of the interphalangeal of the thumb. The orthosis acts both as an antalgic product and as a means for preventing aggravation, such as for example a luxation.

It goes without saying that the invention is not limited to the embodiments described above as examples, but that on the contrary it encompasses all alternative embodiments.

The invention claimed is:

1. An orthosis intended to be placed on a hand of a user, in particular to treat rhizarthrosis, comprising:
a supporting member having a general shape of a horse saddle, having an inner flange and an outer flange connected by a curved U-shaped junction band, the inner and outer flanges arranged opposite one another and spaced apart by the junction band, the supporting member being arranged to be able to be placed at a thumb-index commissure with the inner flange configured for placement against a palm and the outer flange configured for placement against a back surface of the hand, the junction band configured for curving around a medial portion of a proximal phalange of a thumb and a lateral portion of a proximal phalange of an index finger in order to immobilize a metacarpal bone and enable a spacing to be maintained between the thumb and the index finger;
a strap to be placed around the hand and the supporting member, so as to retain said supporting member, the orthosis being arranged such that a metacarpal bone of the thumb is trapped inside the orthosis between the strap and the supporting member;
a rigid dorsal rod connected to the supporting member and/or the strap;
a rigid palmar strip associated with the strap;
wherein the orthosis is arranged such that a column of the thumb is trapped between the dorsal rod and the palmar strip.

2. The orthosis according to claim 1, wherein the dorsal rod has a generally flat lower surface and, in a usage position, said rod extends over a back surface of the hand substantially in an extension of the outer flange of the supporting member, the lower surface bearing against a back surface of the hand.

3. The orthosis according to claim 2, wherein the dorsal rod is made from a deformable material such that a person can bend or curve the rigid rod so as to place a wrist slightly flexed, in the usage position of the orthosis.

4. The orthosis according to claim 2, wherein the supporting member comprises a housing formed in its outer flange and intended to receive an end portion of the rigid rod.

5. The orthosis according to claim 1, wherein the supporting member and the strap are two separate pieces.

6. The orthosis according to claim 1, wherein the inner flange of the supporting member is outwardly curved toward a free end thereof.

7. The orthosis according to claim 1, wherein the supporting member is made from a flexible material, including silicone or SEBS (styrene ethylene butylene styrene).

8. The orthosis according to claim 1, wherein the supporting member comprises a rigid U-shaped piece situated substantially at a junction between the inner and outer flanges, said U-shaped piece being able to be deformed so as to modify a spacing between a thumb and an index finger depending on the user's morphology.

9. The orthosis according to claim 1, wherein the strap, when flat, is substantially in the shape of a T that has first and second branches substantially one in the extension of the other intended to surround the hand while being folded down against the back surface of the hand, and a third branch intended to be folded toward the back surface of the hand while passing through the thumb-index commissure and covering the supporting member.

10. The orthosis according to claim 1, wherein the strap has a sufficient size to also surround a wrist, in a usage position.

11. The orthosis according to claim 1, wherein the strap comprises at least one stiffening element which, in a usage position, extends over the back surface of the hand substantially in an extension of the outer flange of the supporting member.

12. The orthosis according to claim 1, wherein the orthosis is arranged so that, when the orthosis is worn by a user, the hand of the user equipped with the orthosis has a slight cubital incline.

13. The orthosis according to claim 1, wherein the palmar strip extends, in the usage position, from an inner side of the hand and forearm substantially along the axis of the forearm, having a sufficient length to extend on either side of the wrist joint, and having a curved shape fitting the relief of the wrist and the palm of the hand.

14. The orthosis according to claim 1, wherein the general shape of a horse saddle forms a substantially hyperbolic paraboloid shape.

15. The orthosis according to claim 1, wherein the supporting member is arranged to be placed between the thumb and the index finger to procure an antalgic effect and assure a range of motion, and is adapted to immobilize an osteoarticular column of the thumb.

16. The orthosis according to claim 1, wherein the inner and outer flanges are generally parallel near the junction band.

17. The orthosis according to claim 1, wherein the inner flange has a free edge joining two end edges of the junction band and forming a central tab.

18. An orthosis intended to be placed on the hand of a user, in particular to treat rhizarthrosis, comprising:
   a supporting member formed from a flexible material and having a general shape of a horse saddle, having an inner flange and an outer flange connected by a curved U-shaped junction band, the inner and outer flanges arranged opposite one another and spaced apart by the junction band, the supporting member being arranged to be able to be placed at a thumb-index commissure with the inner flange configured for placement against a palm and the outer flange configured for placement against a back surface of the hand, the junction band configured for bearing on a proximal phalange of a thumb and on a proximal phalange of an index finger in order to enable a spacing to be maintained between the thumb and the index finger to procure an antalgic effect and assure a range of motion, and adapted to immobilize an osteoarticular column of the thumb;
   a strap to be placed around the hand and the supporting member, so as to retain said supporting member, the orthosis being arranged such that a metacarpal bone of the thumb is trapped inside the orthosis between the strap and the supporting member and the extension of the strap at least extends between an outer edge of the inner flange and an outer edge of the outer flange to cover the entirety of the junction band;
   a rigid dorsal rod connected to the supporting member and/or the strap;
   a rigid palmar strip associated with the strap;
   wherein the orthosis is arranged such that a column of the thumb is trapped between the dorsal rod and the palmar strip.

19. An orthosis adapted to be placed on a hand of a user, in particular to treat rhizarthrosis, comprising:
   a supporting member having a general shape of a horse saddle, having an inner flange and an outer flange connected by a curved U-shaped junction band, the inner and outer flanges arranged opposite one another and spaced apart by the junction band, the supporting member being arranged to be able to be placed at a thumb-index commissure with the inner flange configured for placement against a palm and the outer flange configured for placement against a back surface of the hand, the junction band configured for bearing on a proximal phalange of a thumb and on a proximal phalange of an index finger in order to enable a spacing to be maintained between the thumb and the index finger to procure an antalgic effect and assure a range of motion, and adapted to immobilize an osteoarticular column of the thumb, the inner and outer flanges being generally parallel near the junction band and the inner flange curving outwardly from the junction band toward its free end, and
   a strap that is separate and independently reconfigurable with respect to the supporting member, the strap to be placed around the hand and the supporting member, so as to retain said supporting member, the orthosis being arranged such that a metacarpal bone of the thumb is trapped inside the orthosis between the strap and the supporting member and the strap extends over the entirety of the junction band;
   a rigid dorsal rod connected to the supporting member and/or the strap;
   a rigid palmar strip associated with the strap;
   wherein the orthosis is arranged such that a column of the thumb is trapped between the dorsal rod and the palmar strip.

* * * * *